United States Patent [19]

Sommer et al.

[11] 4,240,965

[45] Dec. 23, 1980

[54] UNSYMMETRICAL PYRROLINO BENZYL QUATERNARY COMPOUNDS

[75] Inventors: Harold Z. Sommer, Havre de Grace; George E. Wicks, Jr., Baltimore, both of Md.

[73] Assignee: The United States of America as represented by the Secretary of the Army, Washington, D.C.

[21] Appl. No.: 701,015

[22] Filed: Jan. 26, 1968

[51] Int. Cl.[3] .............................................. C07D 207/24

[52] U.S. Cl. ................................ 260/326.41; 424/274

[58] Field of Search ............ 260/482 C, 313.1, 326.41; 424/274

[56] References Cited

U.S. PATENT DOCUMENTS 3,188,955 6/1965 Brown .................................... 102/24

*Primary Examiner*—Leland A. Sebastian

*Attorney, Agent, or Firm*—Nathan Edelberg; Robert P. Gibson; Harold H. Card, Jr.

[57] ABSTRACT

New chemical compounds, bis-quaternary carbamates, having the generic formula:

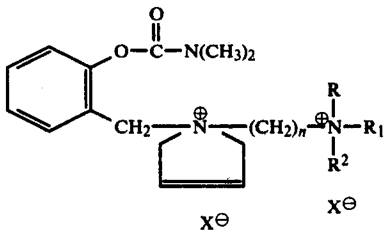

wherein X is one equivalent of an anion selected from nonovalent or polyvalent anions, wherein n is 5-16, and wherein R, $R_1$, $R_2$ are radicals selected from the group consisting of methyl, ethyl, propyl, isopropyl, and butyl, and having utility as toxic agents.

2 Claims, No Drawings

UNSYMMETRICAL PYRROLINO BENZYL QUATERNARY COMPOUNDS

DEDICATORY CLAUSE

The invention described herein may be manufactured, used, and licensed by or for the Government for governmental purposes without the payment to us of any royalty thereon.

This invention relates to the synthesis of new toxic chemical compounds which are useful as chemical warfare agents. More particularly, our invention is concerned with novel compounds produced by means of a quaternizing reaction.

The chemical agents act mostly on the peripheral cholinergic nervous system which includes the motor nerves, the preganglionic fibers, the ganglia, the postganglionic parasympathetic fibers, and neuomuscular functions. The transmission of impulses along a nerve or from nerve fibers to muscle fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers they are attracted by anionic sites in animal tissues, particularly those situated at cell surfaces and interfaces. They can induce physiological responses that mimic or antagonize the action of acetyolcholine as a result of their interaction with the various physiological receptor sites or acetylcholine, especially those at membranes of muscle cells. They also combine with enzymes such as acetylcholinesterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessibility of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings having a bearing on the ease or difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influences association and hydration and may considerably change the solubilities in physiological media. In bis-quaternary and poly-quarternary compounds, the distance between the electric charges must be considered. These factors contribute to govern the rate and reversibility of the chemical reactions involved, and contribute to determine the final physiological responses.

Our chemical agents interfere with the normal process of neuromuscular impulse transmission and thus disrupt the propagation of impulses from nerves to muscles. We have also found these compounds to be extremely toxic at relatively low dose levels in various animals.

The object of this invention is to synthesize new lethal agents useful in chemical warfare in high yields, the agents being well suited for industrial scale manufacture.

Other objects of and uses for the invention will in part be obvious and will in part appear hereinafter in the following detailed description thereof.

Our compounds may be employed in any munition suitable for handling a relatively non-volatile toxic agent such as bombs, shells, spray tanks, rockets, missiles, aerosol generators, and others.

In accordance with our invention, the tertiary aminofunction of an aminocarbamate, such as N-(2-dimethylcarbamoxybenzyl) pyrroline, was quaternized with an ω-bromoalkyltrialkylammonium bromide such as 10-bromodecyltrimethylammonium bromide in a solvent such as acetonitrile. The reaction mixture was allowed to stand at room temperature for relatively prolonged periods of time (3 days to 3 weeks). The addition of a solvent such as acetone caused a viscous oily material to separate. The supernatant solvent mixture was decanted and the remaining oil stirred in a solvent such as acetone. The solvent was decanted and the gummy residue was dissolved in a solvent such as acetonitrile. This solution was treated with decolorizing carbon and concentrated to a few milliliters. The concentrate was placed in an apparatus that was kept under reduced pressure. The resultant white crystalline material constitutes the new compounds of the present invention which may be represented by the following generic formula:

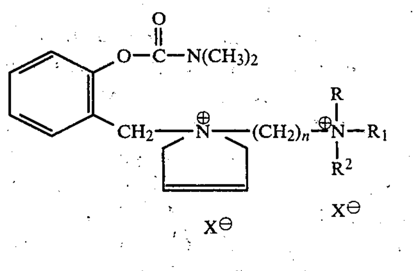

wherein X is one equivalent of an anion selected from monovalent or polyvalent anions, wherein n is 5–16, and wherein R, $R_1$, $R_2$ are radicals selected from the group consisting of methyl, ethyl, propyl, isopropyl, and butyl.

The procedure used for the preparation of the new toxic materials is schematically shown below:

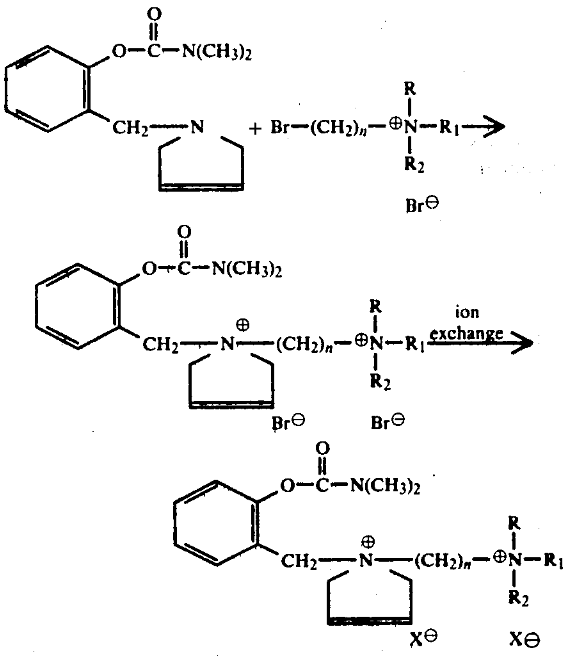

wherein X is a halide ion, preferably bromide, and n, R, $R_1$, $R_2$ are as defined above.

If compounds are desired in which X is other than a halide ion, the above quaternary compounds are treated with the desired acid by simple exchange reactions as set forth below.

EXAMPLE 1

N-(2-Dimethylcarbamoxybenzyl)pyrroline (1.05 g) and 10-bromodecyltrimethylammonium bromide (1.43 g) were dissolved in 10 ml of acetonitrile and the solution allowed to stand for about 72 hours at room temperature. About 50 ml of acetone was then added which caused an oily material to separate. The supernatant solvent mixture was decanted and the remaining oil stirred in about 50 ml of boiling acetone for about 15 minutes. The acetone was decanted, the gummy residue dissolved in about 15 ml of acetonitrile, and the resultant solution treated with decolorizing carbon. The purified solution was concentrated to a few milliliters on a steam bath and the concentrate placed for about 4 hours in an apparatus that was kept under reduced pressure (0.5 mm) at the temperature of boiling chloroform. The product, 1-[N-(2-dimethylcarbamoxybenzyl)pyrrolinio]-10-(N,N,N-trimethylammonio)decane dibromide (1.6 g) was obtained as a deliquescent white crystalline material. Due to the deliquescency, a sample of the compound was converted to and analyzed as the tetraphenylboronate salt. The above dibromide salt was dissolved in water and to this solution an aqueous solution of sodium tetraphenylboron (in molar excess) was added. The solid that formed was collected on a filter, washed a few times with water, and then dried. The tetraphenylboronate salt melted between 86°-88° C.

Analysis for $C_{75}H_{87}B_2N_3O_2$; Calcd: C, 83.1; H, 8.1; N, 3.9. Found: C, 83.2; H, 8.4; H, 8.4; N, 4.0.

| Toxicity IV $LD_{50}$ | |
|---|---|
| Rabbits | Mice |
| 0.006 mg/kg | 0.013 mg/kg |

EXAMPLE 2

A mixture of N-(2-dimethylcarbamoxybenzyl)pyrroline (1.5 g), 8-bromooctyltrimethylammonium bromide (1 g), and 5 ml of acetonitrile was allowed to stand for about 18 days at room temperature. About 50 ml of acetone was then added causing a viscous oily material to separate. The supernatant solvent mixture was decanted and the remaining gum-like material stirred in about 75 ml of acetone for about ½ hour. The acetone was decanted, the gummy residue dissolved in about 20 ml of acetonitrile, and the resultant solution treated with decolorising carbon. The purified solution was concentrated to a few milliliters on a steam bath and the concentrate plated in an apparatus that was kept under reduced pressure (0.5 mm) for about 16 hours at room temperature. Thus, 1.2 g of the product, 1-[N-(2-dimethylcarbamoxybenzyl)pyrrolinio]-8-(N,N,N-trimethylammonio)octane dibromide, was obtained as a deliquescent white solid. Due to the deliquescency, a sample of the compound was converted to and analyzed as the tetraphenylboronate salt. The above dibromide salt was dissolved in water and to this solution an aqueous solution of sodium tetraphenylboron (in molar excess) was added. The solid that formed was collected on a filter, washed a few times with water, and then dried. The tetraphenylboronate salt melted between 115°-120° C.

Analysis for $C_{73}H_{83}B_2N_3O_2$; Calcd: C, 83.0; H, 7.9; N, 4.0. Found: C, 83.1; H, 8.0; N, 4.0.

| Toxicity IV $LD_{50}$ | |
|---|---|
| Rabbits | Mice |
| 0.0046 mg/kg | 0.014 mg/kg |

The compounds that are representative of our invention are listed below by name and chemical structure.

1-[N-(2-dimethylcarbamoxybenzyl)pyrrolinio]-5-(N,N,N-trimethylammonio)pentane dibromide.

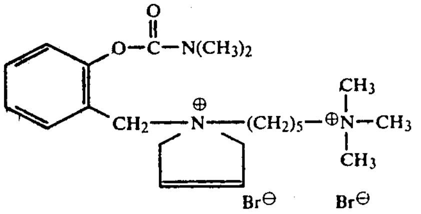

1-[N-(2-dimethylcarbamoxybenzyl)pyrrolinio]-6-(N,N,N-trimethylammonio)hexane dibromide.

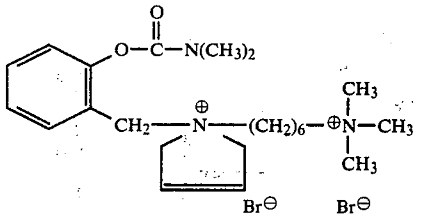

1-[N-(2-dimethylcarbamoxybenzyl)pyrrolinio]-7-(N,N,N-trimethylammonio)heptane dibromide.

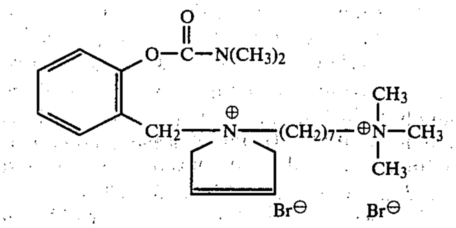

1-[N-(2-dimethylcarbamoxybenzyl)pyrrolinio]-8-(N,N,N-trimethylammonio)octane dibromide.

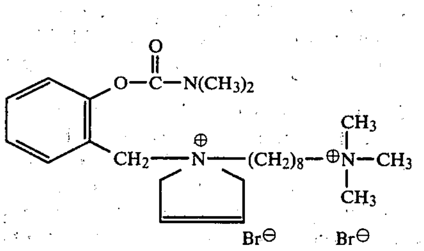

1-[N-(2-dimethylcarbamoxybenzyl)pyrrolinio]-9-(N,N,N-trimethylammonio)nonane dibromide.

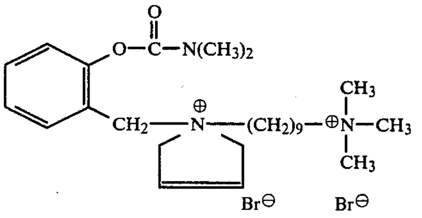

1-[N-(2-dimethylcarbamoxybenzyl)pyrrolinio]-10-(N,N,N-trimethylammonio)decane dibromide.

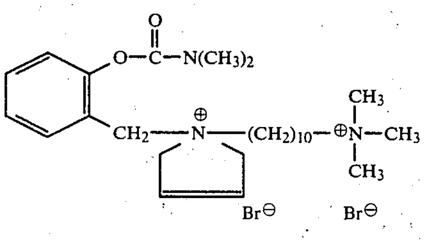

1-[N-(2-dimethylcarbamoxybenzyl)pyrrolinio]-11-(N,N,N-trimethylammonio)undecane dibromide.

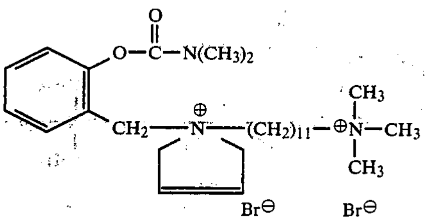

1-[N-(2-dimethylcarbamoxybenzyl)pyrrolinio]-12-(N,N,N-trimethylammonio)-dodecane dibromide.

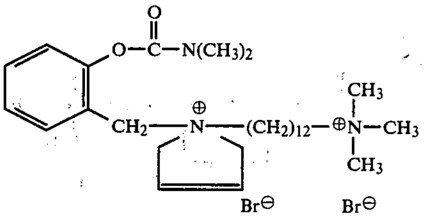

1-[N-(2-dimethylcarbamoxybenzyl)pyrrolinio]-16-(N,N,N-trimethylammonio)hexadecane dibromide.

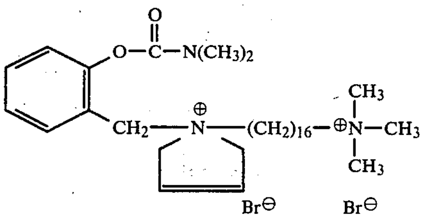

1-[N-(2-dimethylcarbamoxybenzyl)pyrrolinio]-10-(N-ethyl-N,N-dimethylammonio)decane dibromide.

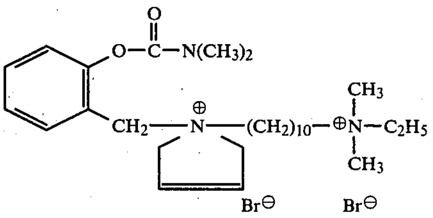

1-[N-(2-dimethylcarbamoxybenzyl)pyrrolinio]-10-(N,N-diethyl-N-methylammonio)decane dibromide.

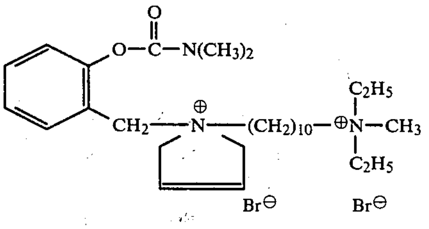

1-[N-(2-dimethylcarbamoxybenzyl)pyrrolinio]-10-(N,N,N-triethylammonio)decane dibromide.

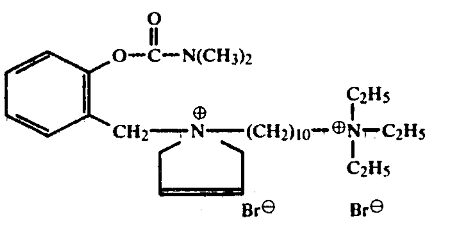

1-[N-(2-dimethylcarbamoxybenzyl)pyrrolinio]-10-(N,N-dimethyl-N-propylammonio)decane dibromide.

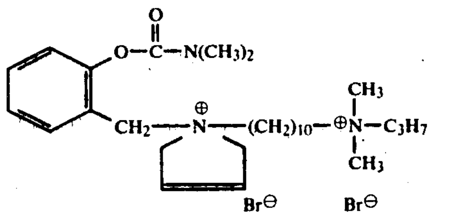

1-[N-(2-dimethylcarbamoxybenzyl)pyrrolinio]-10-(N-ethyl-N-methyl-N-propylammonio)decane dibromide.

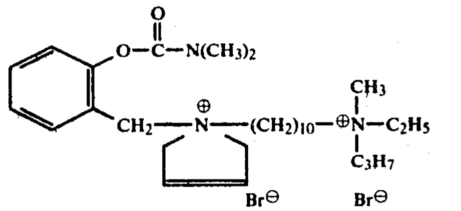

1-[N-(2-dimethylcarbamoxybenzyl)pyrrolinio]-10-(N,N-dimethyl-N-isopropylammonio)decane dibromide.

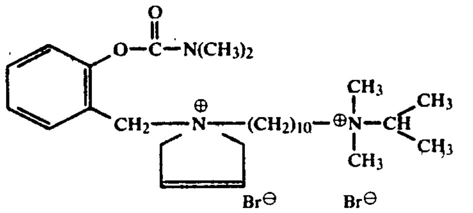

1-[N-(2-dimethylcarbamoxybenzyl)pyrrolino]-10-(N,N-diisopropyl-N-methylammonio)decane dibromide.

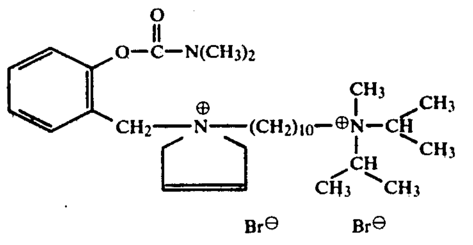

1-[N-(2-dimethylcarbamoxybenzyl)pyrrolinio]-10-(N-butyl-N,N-dimethylammonio)decane dibromide.

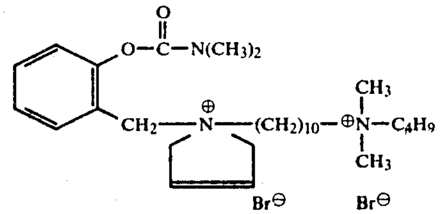

We have shown preferred compounds in which the anion is limited to the halogen moiety, in particular the bromide, since the bromoalkanes are good quaternizing agents. In general, however, it is only necessary that the anions merely have to meet the requirement of being capable of forming a stable salt with the quaternary nitrogen. Thus the halogen ions can be exchanged with other anions of relatively strong monovalent or polyvalent acid by conventional methods. For example, if $X^-$ is a bromide in the final product, a solution of the compound can be treated with a basic ion exchange resin or mixed with silver oxide and subsequently the desired acid is added to the quaternary hydroxide solution. Anions other than the halogens may also be obtained by metathesis with the halide form of the quaternary ammonium compound. Suitable as representations of $X^-$ are the anions hydrogen oxalate, perchlorate, nitrate, tetraphenylboronate, hydrogen sulfate. Representative examples of these additional endproducts are:

1-[N-(2-dimethylcarbamoxybenzyl)pyrrolinio]-8-(N,N,N-trimethylammonio)octane di(hydrogen oxalate);

1-[N-(2-dimethylcarbamoxybenzyl)pyrrolinio]-8-(N,N,N-trimethylammonio)octane diperchlorate;

1-[N-(2-dimethylcarbamoxybenzyl)pyrrolinio]-8-(N,N,N-trimethylammonio)octane dinitrate;

1-[N-(2-dimethylcarbamoxybenzyl)pyrrolinio]-8-(N,N,N-trimethylammonio)octane di(tetraphenylboronate);

1-[N-(2-dimethylcarbamoxybenzyl)pyrrolinio]-8-(N,N,N-trimethylammonio)di(hydrogen sulfate).

We claim:

1. New chemical compounds having the generic formula:

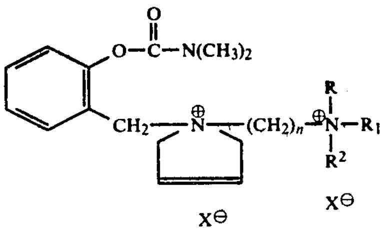

wherein X is one equivalent of an anion selected from the group consisting of monovalent and polyvalent anions, said anions being selected from the group consisting of halide, hydrogen oxalate, perchlorate, nitrate, tetraphenylboronate, and hydrogen sulfate; wherein n is selected from 5-16, and wherein R, $R_1$, $R_2$ are radicals selected from the group consisting of methyl, ethyl, propyl, isopropyl, and butyl.

2. New chemical compounds selected from the group of compounds having the names:

1-[N-(2-dimethylcarbamoxybenzyl)pyrrolinio]-8-(N,N,N-trimethylammonio)octane dibromide; and 1-[N-(2-dimethylcarbamoxybenzyl)pyrrolinio]-10-(N,N,N-trimethylammonio)decane dibromide.

* * * * *